(12) United States Patent
Heske

(10) Patent No.: US 6,387,057 B1
(45) Date of Patent: May 14, 2002

(54) DEVICE FOR GENTLY REMOVING TISSUE FROM ANIMAL OR HUMAN TISSUE

(76) Inventor: Norbert Heske, Am Brand 1, D-82299 Türkenfeld (DE)

( * ) Notice: Subject to any disclaimer, the term of this patent is extended or adjusted under 35 U.S.C. 154(b) by 0 days.

(21) Appl. No.: 09/869,837
(22) PCT Filed: Nov. 7, 2000
(86) PCT No.: PCT/EP00/10987
§ 371 Date: Sep. 7, 2001
§ 102(e) Date: Sep. 7, 2001
(87) PCT Pub. No.: WO01/34046
PCT Pub. Date: May 17, 2001

(30) Foreign Application Priority Data

Nov. 9, 1999 (DE) .......................................... 199 53 938

(51) Int. Cl.$^7$ ................................................ A61B 5/00
(52) U.S. Cl. .................................................... 600/565
(58) Field of Search ................................ 600/564–567; 606/42, 44, 46, 49

(56) References Cited

U.S. PATENT DOCUMENTS 4,301,802 A * 11/1981 Poler ........................... 128/303
5,019,036 A * 5/1991 Stahl ............................ 604/22
5,133,360 A * 7/1992 Spears ........................ 128/749
5,797,907 A * 8/1998 Clement ....................... 600/49

* cited by examiner

Primary Examiner—Max Hindenburg
(74) Attorney, Agent, or Firm—Antonelli, Terry, Stout & Kraus, LLP

(57) ABSTRACT

Disclosed is a device for the non-invasive removal of tissue from animal or human tissue, which device has a hollow needle that is provided with a hollow channel.

Figure 1:
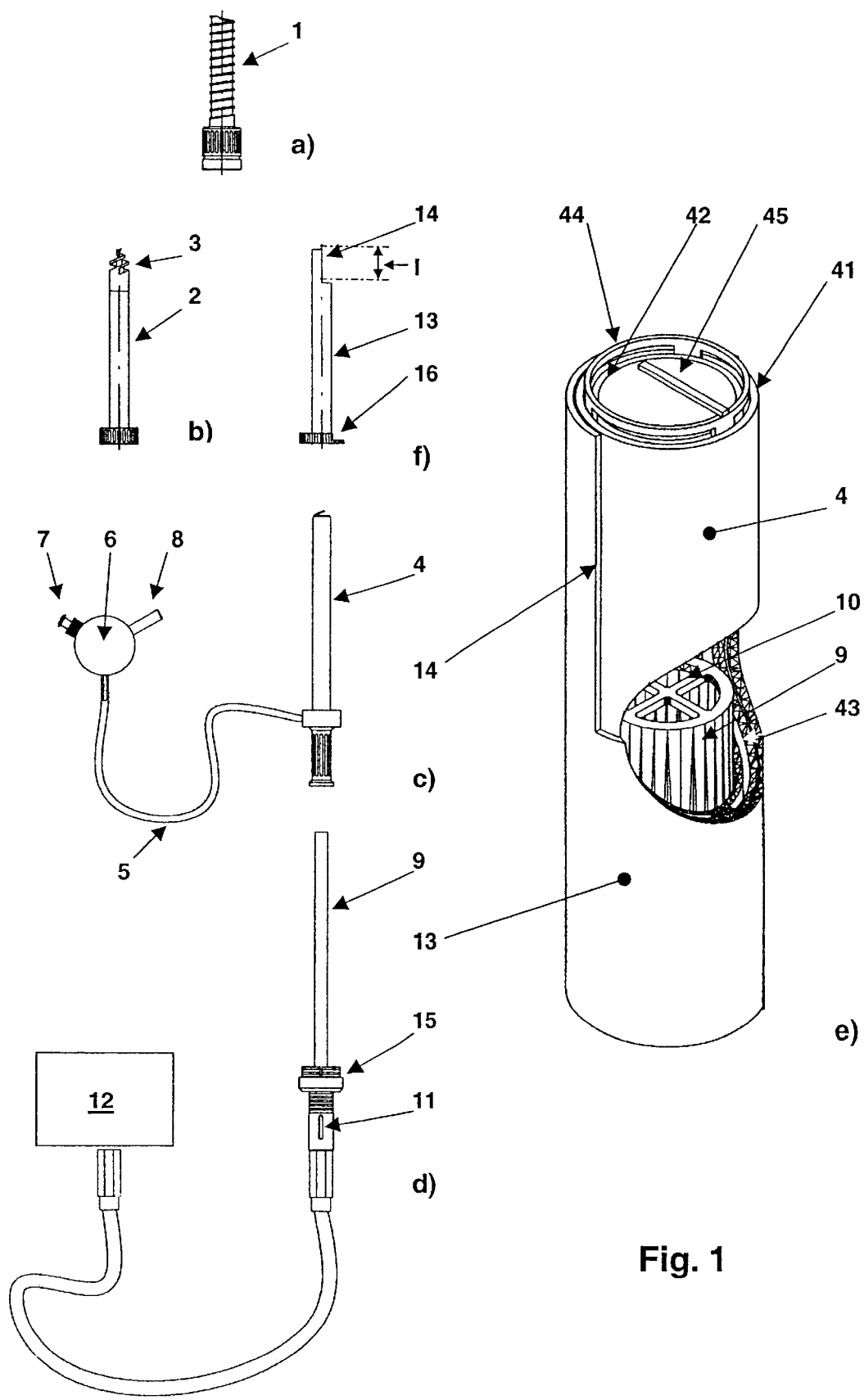

The invention is distinguished by the hollow needle being designed as a multi-wall hollow needle and being provided with at least two hollow needle walls enclosing at least one intermediate space which is designed open at the distal end, by a cutting wire suppliable with electric energy extending at the distal end from the intermediate space, by a supply line being provided for the material flow at the proximal end in the intermediate space of the multi-wall hollow needle and the intermediate space and the supply line being designed in such a manner that the material flow flows through the intermediate space and exits at the distal end, and by a vacuum source being connectable at the proximal end of the hollow channel of the multi-wall hollow needle.

22 Claims, 1 Drawing Sheet

DEVICE FOR GENTLY REMOVING TISSUE FROM ANIMAL OR HUMAN TISSUE

TECHNICAL FIELD

The present invention relates to a device for the minimal-invasive removal of tissue from animal or human tissue, which device has a hollow needle provided with a hollow channel.

State of the Art

There are numerous known different methods and devices employed to examine tissue for the selective removal of tissue from animal or human bodies. Starting with the familiar classical surgical procedure using a scalpel to provide a passage to the to-be-severed and to-be-examined tissue area in order to sever this tissue area with selective cuts and to remove it from the body through the work passage, one proceeded, due to the many drawbacks related to this classical surgical procedure, to design a suited instrument for minimal-invasive surgery. Although, it is possible to extract sufficiently large amounts of tissue material from the body for examination with the classical method, the surgery and the related tissue sections involve irreversible tissue irritation, which takes much time to heal. Moreover, there is the danger of cell displacement in that tissue that may be tumorous is severed and removed through the work passage is carried to nonmalignant tissue.

In order to rule out the drawbacks described above, punch biopsy devices are known which permit removing tissue at selected intracorporal tissue areas by means of a single incision with a needle. This comprises a combination of a hollow needle having a mandrel running inside the hollow needle. This mandrel is provided with a recess at the distal end in which tissue, that can be severed with the aid of the sharpened distal end of the hollow needle, can be stored. Although this type of tissue removal is minimal-invasive and involves only minor tissue irritation caused by the injection of the needle arrangement into the body and the needle arrangement largely rules out the problem of cell displacement because the tissue severed in the to-be-examined tissue is enclosed in order to be safely removed from the body. The disadvantage of the known punch biopsy, however, is that only a small amount of tissue can be removed with a single incision of the hollow needle. Although the amount of the to-be-examined tissue can be increased by multiple successive biopsies, the tissue is greatly stressed and irritated by the numerous incisions. On the other hand, hollow needle arrangements with increasingly larger cross sections can be resorted to, however, this raises the danger of bleeding and consequently hematoma formation leading to unavoidable side effects.

DESCRIPTION OF THE INVENTION

The object of the present invention is to design a device for minimal-invasive removal of tissue from animal or human tissue, which device has a hollow needle provided with a hollow channel, in such a manner that the afore-described drawbacks can largely be prevented. In particular, the aim is to reduce to a minimum irreversible tissue irritation caused by the surgical operation by means of a minimal-invasive surgical procedure in the to-be-examined tissue area. Injury to the tissue cells from the surgical procedure should also be minimized and the danger of bleeding should be reduced to a minimum. Despite the minimal-invasive surgical procedure, it should still be possible to remove from inside the body a minimum amount of tissue material required for unequivocal determination of the tissue respectively examination of the tissue.

The solution to the object of the present invention is given in claim 1. Advantageous features that further develop the inventive idea are the subject matter of the subclaims and are disclosed in the description as well as in the preferred embodiment with reference to the accompanying drawing.

An element of the present invention is to design a device for minimal-invasive removal of tissue from animal or human tissue, which has a hollow needle provided with a hollow channel, in such a manner that the hollow needle is designed as a multi-wall hollow needle and is provided with at least two hollow needle walls enclosing at least one intermediate space which is designed open at the distal end. Extending at the distal end from this intermediate space is a cutting wire that can be supplied with electric energy and is preferably designed with a shape corresponding to the contour of the cross section of the intermediate space and is located at a distance opposite this intermediate space. A supply line for a material flow ends in the proximal end of the intermediate space of the multi-wall hollow needle, with the supply line and the intermediate space being connected and designed in such a manner that that the material flow flows through the intermediate space and exits at the distal end. Preferably an electrically nonconductive scavenging fluid, for example a glycol solution, is employed as the material flow. Moreover, the scavenging fluid should possess approximately the same mineral content as the human or animal tissue fluid or at least be chemically inert so that the intracorporal scavenging has no negative influence on the mineral content of the surrounding tissue.

Gases, for instance inert gases such as argon can also be used. Finally a vacuum source can be connected at the proximal end of the hollow channel of the preferably double-walled multi-wall hollow needle.

The multi-wall hollow needle preferably designed as a double-walled hollow cylinder is preferably provided with an exterior contour matching the interior contour of a hollow channel designed as a sluice serving as the work channel for intracorporal insertion of endosurgical instruments into the body, thus also for insertion of the invented hollow needle. To keep tissue and cell irritation to a minimum when inserting such a type of sluice, for example, through the various layers of the skin down to the to-be-examined tissue area, there are known sluice arrangements which are provided with a helical screw thread on their exterior and a tapering-to-a-tip screw thread at the distal end, with the screw tip being the distal end part of a mandrel extending through the sluice, which is led through for the purpose of entering the sluice arrangement inside the body. Such a type of sluice arrangement is described in DE 199 35 976.8. The particular advantage of such a type of sluice arrangement is that the tissue is not cut when the sluice arrangement is inserted, but rather is dilated by the spiral-like designed tip so that natural interfaces in the tissue respectively in the cell structures entered by the distal screw tip give way thus permitting to largely avoid severing blood vessels, nerves or cells. Positioning such a sluice can be controlled using ultrasonic, X-ray or MR monitoring methods to check the position relative to the to-be-examined tissue area.

If the sluice arrangement is positioned accordingly and the central mandrel is removed from the hollow channel, a work channel is created through which the invented tissue removal device can be placed accordingly. Fundamentally, leading the invented tissue removal device described in the following through other work channels or the work channel can even be completely obviated. This however is connected with distinct drawbacks during the surgical operation. For selective tissue removal, the multi-wall hollow needle is preferably double walled and designed as a hollow cylinder whose needle length is selected larger than the length of the sluice so that the multi-wall hollow needle extends out of the sluice at the distal end and can enter the to-be-examined tissue area accordingly. Entry of the distal end of the multi-wall hollow needle occurring into the tissue area is distinguished, in particular, by the cutting wire, which is disposed immediately before the open distal end of the intermediate space of the multi-wall hollow needle and whose shape essentially corresponds to that of the cross section of the intermediate space and is positioned at a slight distance therefrom, having electric energy, preferably HF current, applied to it and being heated thereby. The tissue coming into contact with the cutting wire is thermally severed and simultaneously a coagulation process sets in which prevents later bleeding. So to say the purpose of the cutting wire is a sort of high-frequency surgical cutting device which immediately protects the cell tissues from bleeding further during severing by means of thermal coagulation. Severing of the to-be-severed tissue can also occur by means of an erosion method, i.e. the tissue does not come into immediate contact with the cutting wire but rather is thermally denatured by the sparks discharged by the high electric voltages at the cutting wire. The sparks cause a plasma to form which leads to the desired erosion effects. Also feasible is a three-walled design of the multi-wall hollow needle, which contains two intermediate spaces, through one of which a scavenging fluid is led and through the other of which a gas is led at the distal end, which contributes to the selective plasma formation.

As a result of the distal advancing of the multi-wall hollow needle, the cutting wire, which is preferably designed like a sort of full circle, severs a tissue volume and conveys it into the hollow needle, which has the shape of a full cylinder. In order for the tissue severed from the other tissue to be able to completely enter into the interior of the multi-wall hollow needle, the hollow channel of the multi-wall hollow needle is connected to a vacuum source, by means of which all severed tissue areas are able to enter the interior of the multi-wall hollow needle. Moreover, a material flow, preferably a glycol solution, which is supplied to the hollow needle at the proximal end via a supply line exits from the distal end of the intermediate space. The glycol solution is able to considerably support the severing process and removal of the severed tissue areas into the inside of the hollow channel. Furthermore, the glycol solution ensures the desired cooling of the tissue surrounding the heated cutting wire, whereby minimizing the heat input on the surrounding tissue is minimized.

In addition to the circular design of the cutting wire, it is provided with a cutting wire bridge which is directed to the middle of the hollow channel surrounded by the multi-wall designed hollow needle. When inserting the cutting wire ring attached to the distal end of the multi-wall hollow needle into the tissue, the tissue is cut open by the cutting wire bridge in longitudinal direction to the severed tissue cylinder at least half of the severed cylinder diameter. If a desired incision depth is reached inside the tissue by corresponding insertion of the multi-wall hollow needle into the tissue area, the multi-wall hollow needle including the cutting wire arrangement is turned about the longitudinal axis of the hollow needle. As a result, the cutting wire bridge severs the tissue core located inside the multi-wall hollow needle completely on the distal side from the remaining tissue. The tissue sample severed from the remaining tissue inside the body in this manner is kept inside the hollow channel by means of the vacuum and can be easily removed from inside the body through the work channel of the sluice.

In order for the tissue sample completely severed inside the body not to be uncontrollably sucked away at the proximal end by the vacuum inside of the hollow channel of the multi-wall hollow needle, the vacuum source is connected to a single-walled hollow needle at whose distal end a meshwork or a similarly designed arrangement is provided so that only predominantly fluid parts or gas parts can be aspired through the hollow needle at the distal end of the single-walled hollow needle and severed solid material parts such as the tissue sample itself are kept in front of the hollow needle at the distal end by the meshwork. For this purpose, during the cutting process, the hollow needle is inserted at the proximal end into the hollow channel of the double-walled multi-wall hollow needle. The depth of entry of the single-walled hollow needle into the double-walled multi-wall hollow needle is selected in such a manner that there is sufficient distance between the distal end of the double-walled multi-wall hollow needle and the distal end of the single-walled hollow needle connected to the vacuum source so that a sufficient amount of tissue material can be drawn inside the hollow channel. In order to avoid cell displacement through healthy tissue areas, it is advantageous if the reception volume of the hollow channel of the double-walled multi-wall hollow needle is larger than the actual removed tissue volume. The vacuum inside the hollow channel holds the removed sample of tissue fast on the single-walled hollow needle thereby permitting removal of the single-walled hollow needle with the tissue core located at the distal end of the hollow needle.

If a second removal of tissue is required at another site in the tissue, renewed removal can be carried out using the thermal cutting device by changing the angle of the sluice.

If one replaces the sluice, which as previously described is designed with an exterior screw thread, with a hollow needle which is provided with a recess at the distal end, for example in the form of a cut out section extending halfway to the axis of the hollow channel, repeated tissue removal in the radial surrounding of the hollow needle is possible without moving the sluice respectively the work channel, thereby permitting further reduction of possible irritations. This occurs in such a manner that the multi-wall hollow needle is pushed into the suitable prepared hollow needle maximally to the proximal edge of the cut out section. A vacuum applied inside the multi-wall hollow needle ensures that the tissue material, which lies radially adjacent to the distal end of the hollow needle immediately opposite the cut out section, is drawn laterally into the hollow needle. Subsequently the multi-wall hollow needle is pushed toward the distal end with the heated cutting wire and the tissue material drawn into the cut out section is severed and is conveyed outside the body by means of the previously described method. This tissue severing procedure can be repeated accordingly after the hollow needle is slightly turned about its longitudinal axis. Turning the hollow needle occurs without any tissue irritation.

With the afore-described method, large pieces of tissue volume can be removed from the body piecemeal. The removal procedure occurs preferably under visual monitoring, for example by means of X-ray observation, so that selected tissue areas about the hollow needle arrangement can be removed in a minimal invasive manner.

In order to supply the cutting wire emerging from the distal end of the double-walled hollow channel with electric energy, the cutting wire is connected via an electric connection running at the proximal end inside the intermediate space. The electric connection runs at the proximal end via the supply line through which the intermediate space is supplied with glycol solution. As both the scavenging fluid and the electric lead run through one and the same intermediate space, it is absolutely necessary that the scavenging fluid is not electrically conductive. Corresponding variation of the cutting current, which is supplied to the cutting wire like a HF current, permits selective coagulation at the cutting site, which denatures the tissue and in this way prevents later bleeding as well as cell displacement.

After successful removal of tissue, the sluice acting as the work channel can be removed. The essentially dilated tissue assumes its original position again and can quickly heal.

A particular advantage for subsequent tissue analysis is the partial longitudinal section inside the tissue sample, severed as a full cylinder, due to the cutting-wire bridge, because the longitudinal section permits as a marking aid later unequivocal allocation to the original location in the to-be-examined tissue area before cutting.

BRIEF DESCRIPTION OF THE INVENTION

The present invention is made more apparent in the following without the intention of limiting the scope or spirit of the general inventive idea using preferred embodiments with reference to the accompanying drawing by way of illustration.

FIGS. 1a to f show diagrams of the individual components for tissue removal.

FIG. 1a shows a greatly simplified diagram of a sluice hollow needle 1 provided with a helical exterior screw thread which is completely filled by a mandrel 2, depicted in FIG. 1b, for insertion into, for example, the layers of skin of a human body. At its distal tip, the mandrel 2 is provided with a conically tapering screw thread 3 which permits non-invasive dilating and insertion of the sluice 1 into an intracorporal area. The hollow needle arrangements shown in FIGS. 1a and 1b are described in detail in DE 199 35 976.8.

When the sluice 1 is correctly positioned with the distal open end at a to-be-examined tissue area, the double-walled multi-wall hollow needle 4 according to FIG. 1c is inserted into the sluice 1. The distal end area of the hollow needle 4 is shown in detail in FIG. 1e. The cylinder-shaped multi-wall hollow needle 4 is provided with an interior wall 42 and exterior wall 41 which enclose an intermediate space 43 (shown hatched in FIG. 1e). A circular cutting wire 44 which is provided with a cutting wire bridge extending to the middle of the hollow channel of the multi-wall hollow needle 4 extends from the intermediate space 43 which is designed with an open distal end. In order to electrically contact the cutting wire 44 and the cutting wire bridge 45, the cutting wire 44 and the cutting wire bridge 45 are connected to an electric lead which runs through the intermediate space 43 at the proximal end.

At the proximal side, the double-walled multi-wall hollow needle 4 is connected to a tube-like supply line 5 which ends with one end in the intermediate space 43 and with its other end, it is connected to an adapter piece 6 which is provided with two connection areas 7, 8. Via the connection area 7, a glycol solution is fed into the supply line 5 through which the glycol solution enters the intermediate space 43 and exits at the distal end area of the hollow needle 4. The electric lead which ends in the connection area 8 in order to be connected there to a corresponding HF energy source also runs via the supply line 5.

The multi-wall hollow needle 4 is designed open at both the distal end and the proximal end so that a single-walled hollow needle 9 can be inserted into the multi-wall hollow needle 4 from the proximal end. The hollow needle 9 is connected to a vacuum source 12, which is not shown in detail. The distal end of the hollow needle 9 is provided with a meshwork 10 as shown in FIG. 1e. Meshwork 10 prevents the tissue material sucked into the multi-wall hollow needle 4 from also escaping through the hollow needle 9.

The arrangement of the double-walled multi-wall hollow needle 4 and the single-walled hollow needle 9 depicted in FIG. 1e shows the state with the single-walled hollow needle 9 completely inserted into the double-walled multi-wall hollow needle 4. Sufficient room is provided inside the multi-wall hollow needle 4 to convey severed tissue material into the multi-wall hollow needle 4.

Finally the hollow needle 9 connected to the vacuum source 12 is provided with a sliding switch 11 with which the vacuum inside the hollow needle 9 can be quickly reduced, which is necessary in order to easily remove the severed tissue sample removed from hollow needle 4 from the distal end of the hollow needle 9.

FIG. 1f shows an additional hollow needle 13 which is provided with a cut out section 14 at the distal end. This cut out section extends over half the circumference of the hollow needle and has a length l of approximately 1–2 cm. The hollow needle is utilized when additional tissue material which lies radially adjacent to the hollow needle arrangement is to be removed. The hollow needle 13 is provided with a length in such a manner that at the distal end, the hollow needle extends at least with its cut section 14 beyond sluice 1. At the proximal end, the hollow needle 13 is provided with a mechanical stop 16 which limits the maximum insertion depth of the hollow needle 13 into the sluice.

In FIG. 1e, the multi-wall hollow needle 4 is completely inserted in the hollow needle 13. A section through the hollow needle arrangement showing the hollow needle inside the multi-wall needle 4 is drawn in only for better depiction. Sluice 1 is not shown in FIG. 1e.

A distance ring 15 which is provided at the hollow needle 9 ensures a mechanical stop to the proximal end of the multi-wall hollow needle 4 and is provided with a distance ring thickness in such a manner that the hollow needle 9 reaches maximally to the proximal end of the cut out section 14, because in this manner it is ensured that the severed tissue can be drawn completely into the multi-wall hollow needle 4 over the length l. The distance ring 15 can also be removed from the hollow needle 9 permitting the hollow needle 9 to penetrate deeper into the multi-wall hollow needle 4. This is particularly advantageous if less tissue volume is to be removed than if the distance ring 15 is provided.

Removal of tissue with the aid of the hollow needle 13 occurs in the following manner. After hollow needle 13 with the multi-wall hollow needle 4 located inside it has been brought into a respective tissue area, the tissue area is severed in the longitudinal direction to the length of the hollow needle either by means of the hollow needle arrangement and removed outside the body or at least it is dilated. Now the tissue area extending radially about the distal end region of the hollow needle arrangement has to be removed in a minimal invasive manner. For this purpose, the multi-wall hollow needle 4 is pushed toward the proximal end in such a manner that the cut out section 14 is free. The tissue lying adjacent to the cut out section 14 is drawn into the hollow needle 13 by the vacuum through hollow needle 9, which is located inside the multi-wall hollow needle 4. Subsequently the multi-wall hollow needle is pushed toward the distal end and the cutting wire severs the tissue drawn into the hollow needle 13. The severed tissue is drawn into the multi-wall hollow needle 4. Then the tissue is removed outside the body accordingly.

The tissue severing process is now repeated after the hollow needle 13 is turned preferably a quarter turn in longitudinal direction to the axis of the hollow needle.

In this manner, the tissue lying radially around the hollow needle arrangement can be removed in a non-invasive manner without permanently damaging the surrounding tissue.

LIST OF REFERENCE NUMBERS

1 Sluice
2 Mandrel
3 Screw thread
4 Multi-wall hollow needle
42 Interior wall
41 Exterior wall
43 Intermediate space
44 Cutting wire
45 Cutting wire bridge
46 Electric lead
5 Supply line
6 Adapter piece
7,8 Connection areas
9 Hollow needle
10 Meshwork
11 Sliding switch
12 Vacuum source
13 Hollow needle
14 Cut out section
15 Distance ring

What is claimed is:

1. A device for the non-invasive removal of tissue from animal or human tissue, comprising:
   a hollow needle with a hollow channel, wherein the hollow needle is as a multi-wall hollow needle and has at least two hollow needle walls enclosing at least one intermediate space which is open at a distal end;
   a cutting wire, suppliable with electrical energy and extending at the distal end from the intermediate space;
   a supply line provided for the material flow at the proximal end in said intermediate space of said multi-wall hollow needle, said intermediate space and said supply line providing the material flow through the intermediate space and an exiting of the material flow at the distal end; and
   a vacuum source connectable at the proximal end of said hollow channel of said multi-wall hollow needle.

2. The device according to claim 1, wherein:
   the cutting wire is suppliable with electrical energy via an electrical connection which runs through said intermediate space in a proximal direction.

3. The device according to claim 2, wherein:
   at the proximal end, the electrical connection runs through the supply line through which said material flow is conveyable into the intermediate space and is connected to an electrical energy source.

4. The device according to claim 1, wherein:
   the cutting wire extending from the distal end of the intermediate space has a shape matched to a shape of a cross section of the intermediate space.

5. The device according to claim 1, wherein said cutting wire has a cutting wire section which extends from said intermediate space into the hollow channel.

6. The device according to claim 1, wherein:
   the multi-wall hollow needle has a circular cross section and the intermediate space has a ring-shaped cross section.

7. The device according to claim 6, wherein:
   the cutting wire extending from the intermediate space is circular-shaped and a cutting wire bridge is directed from the circular-shaped cutting wire to a middle of the hollow channel.

8. The device according to claim 1, wherein:
   the vacuum source is connected to a single-walled hollow needle which is provided with an exterior diameter corresponding to an interior diameter of the hollow channel of the multi-wall hollow needle.

9. The device according to claim 8, wherein:
   a meshwork is provided at the distal end of the single-walled hollow needle connected to the vacuum source to provide that predominantly fluid and gas parts are aspirable and that solid parts remain at the distal end of the hollow needle.

10. The device according to claim 8, wherein:
    a ventilation device is provided on the single-walled hollow needle to reduce the vacuum prevailing inside the hollow needle.

11. The device according to claim 1, wherein:
    the material flow comprises a fluid.

12. The device according to claim 1, wherein:
    the multi-wall hollow needle is provided with an exterior shape matching an interior shape of a work channel which is insertable into layers of tissue in order to guide the multi-wall hollow needle intracorporally to a to-be-severed area of tissue.

13. The device according to claim 1, wherein:
    a hollow needle is provided into which the multi-wall hollow needle is insertable and at the distal end thereof a cut out section is provided.

14. The device according to claim 12, wherein:
    the cut out section is a cut out section in a wall of the hollow needle extending over half of a circumference edge of the hollow needle.

15. The device according to claim 2, wherein:
    the cutting wire extending from the distal end of the intermediate space has a shape matched to a shape of a cross section of the intermediate space.

16. The device according to claim 2, wherein:
    the cutting wire has a cutting wire section which extends from the intermediate space into the hollow channel.

17. The device according to claim 2, wherein:
    the multi-wall hollow needle has a circular cross section and the intermediate space has a ring-shaped cross section.

18. The device according to claim 2, wherein:
    the cutting wire extending from the intermediate space is circular-shaped and a cutting wire bridge is directed from the circular-shaped cutting wire to a middle of the hollow channel.

19. The device according to claim 8, wherein:
    a ventilation device is provided on the single-walled hollow needle to reduce the vacuum prevailing inside said hollow needle.

20. The device according to claim 2, wherein:
    the material flow comprises a fluid.

21. The device according to claim 2, wherein:

at the proximal end, the electrical connection runs through the supply line, through which the material flow is conveyed into the intermediate space, and is connected to an electrical energy source.

22. The device according to claim 3, wherein:

the cutting wire extending from the distal end of the intermediate space has a shape matched to a shape of a cross section of the intermediate space.

* * * * *